United States Patent
Kim et al.

(10) Patent No.: US 6,863,684 B2
(45) Date of Patent: Mar. 8, 2005

(54) DEFORMABLE SCAFFOLDING MULTICELLULAR STENT

(75) Inventors: Steven W. Kim, San Jose, CA (US); Joshua Makower, Los Altos, CA (US); J. Christopher Flaherty, Los Altos, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 11 days.

(21) Appl. No.: 10/617,105

(22) Filed: Jul. 9, 2003

(65) Prior Publication Data

US 2004/0015225 A1 Jan. 22, 2004

Related U.S. Application Data

(60) Division of application No. 09/933,295, filed on Aug. 20, 2001, now Pat. No. 6,613,081, which is a division of application No. 09/089,032, filed on Jun. 2, 1998, now Pat. No. 6,330,884, which is a continuation-in-part of application No. 08/970,694, filed on Nov. 14, 1997, now Pat. No. 6,432,127.

(51) Int. Cl.[7] .................................................. A61F 2/06
(52) U.S. Cl. ..................................................... 623/1.15
(58) Field of Search ............................... 623/1.15–1.22, 623/23.7, 23.71, 1.1, 1.11; 606/108, 191, 194–198; 604/96, 104

(56) References Cited

U.S. PATENT DOCUMENTS

| 4,739,768 A | 4/1988 | Engelson |
| 4,800,882 A | 1/1989 | Gianturco |
| 4,861,336 A | 8/1989 | Helzel |
| 5,035,706 A | 7/1991 | Giantureo et al. |
| 5,135,536 A | 8/1992 | Hillstead |

(List continued on next page.)

FOREIGN PATENT DOCUMENTS

| DE | 29 702671 | 2/1997 |
| EP | 749729 | 2/1993 |

(List continued on next page.)

OTHER PUBLICATIONS

Jomed, *"Jostent Coronary Stent Graft: The Best of Both Worlds"* (1991), 1–4.

(List continued on next page.)

*Primary Examiner*—David J. Isabella (57) ABSTRACT

A plastically deformable stent for implantation within a body passage includes a plurality of cylindrical segments, and a plurality of connectors extending between adjacent segments. Each segment has an alternating pattern of curvilinear elements extending about its circumference, including first and second sets of curvilinear elements having different resistances to expansion, and preferably defining "U" shapes with alternating lengths that are connected to one another to define a substantially sinusoidal pattern. The connectors define a sinusoidal shape adapted to extend and compress axially substantially evenly when the adjacent segments are subjected to bending. The stent may be delivered on a device including an elongate member with a nose cone, an expandable member, and a proximal shoulder thereon, and an outer sheath for slidably receiving the elongate member therein. The outer sheath and/or nose cone may have perfusion holes for allowing continued perfusion of fluid during stent delivery. The device may be used in a method for implanting a stent within a curved region of a body passage, particularly for creating and/or maintaining a channel connecting a vein to an adjacent artery, preferably in the coronary system.

6 Claims, 7 Drawing Sheets

U.S. PATENT DOCUMENTS

| | | |
|---|---|---|
| 5,282,824 A | 2/1994 | Giantureo |
| 5,314,472 A | 5/1994 | Fontaine |
| 5,366,490 A | 11/1994 | Edwards et al. |
| 5,383,892 A | 1/1995 | Cardon et al. |
| 5,507,767 A | 4/1996 | Maeda et al. |
| 5,527,354 A | 6/1996 | Fontaine et al. |
| 5,540,712 A | 7/1996 | Kleshinski et al. |
| 5,545,210 A | 8/1996 | Hess et al. |
| 5,573,508 A | 11/1996 | Thornton |
| 5,591,197 A | 1/1997 | Orth et al. |
| 5,591,198 A | 1/1997 | Boyle et al. |
| 5,591,230 A | 1/1997 | Horn et al. |
| 5,603,698 A | 2/1997 | Roberts et al. |
| 5,628,754 A | 5/1997 | Shevlin et al. |
| 5,676,670 A | 10/1997 | Kim |
| 5,697,971 A | 12/1997 | Fischell et al. |
| 5,702,418 A | 12/1997 | Ravenscroft |
| 5,702,419 A | 12/1997 | Berry et al. |
| 5,707,386 A | 1/1998 | Schnepp-Pesch et al. |
| 5,713,917 A | 2/1998 | Leonhardt et al. |
| 5,713,949 A | 2/1998 | Jayaraman |
| 5,716,393 A | 2/1998 | Linderberg et al. |
| 5,725,572 A | 3/1998 | Lam et al. |
| 5,733,267 A | 3/1998 | Del Toro |
| 5,733,325 A | 3/1998 | Robinson et al. |
| 5,735,893 A | 4/1998 | Lau et al. |
| 5,741,327 A | 4/1998 | Frantzen |
| 5,741,333 A | 4/1998 | Frid |
| 5,755,769 A | 5/1998 | Richard et al. |
| 5,755,771 A | 5/1998 | Penn et al. |
| 5,755,775 A | 5/1998 | Trerotola et al. |
| 5,755,776 A | 5/1998 | Al-Saadon |
| 5,755,781 A | 5/1998 | Jayaraman |
| 5,759,186 A | 6/1998 | Bachmann et al. |
| 5,759,192 A | 6/1998 | Saunders |
| 5,766,203 A | 6/1998 | Imran et al. |
| 5,772,669 A | 6/1998 | Vrba |
| 5,776,140 A | 7/1998 | Cottone |
| 5,776,161 A | 7/1998 | Globerman |
| 5,776,181 A | 7/1998 | Lee et al. |
| 5,776,183 A | 7/1998 | Kanesaka et al. |
| 5,779,731 A | 7/1998 | Leavitt |
| 5,782,855 A | 7/1998 | Lau et al. |
| 5,782,906 A | 7/1998 | Marshall et al. |
| 5,792,144 A | 8/1998 | Fischell et al. |
| 5,797,920 A | 8/1998 | Kim |
| 5,800,517 A | 9/1998 | Anderson et al. |
| 5,800,522 A | 9/1998 | Campbell et al. |
| 5,810,837 A | 9/1998 | Hoffmann et al. |
| 5,810,872 A | 9/1998 | Kanesaka et al. |
| 5,814,063 A | 9/1998 | Freitag |
| 5,815,904 A | 10/1998 | Clubb et al. |
| 5,843,027 A | 12/1998 | Stone et al. |
| 5,855,600 A | 1/1999 | Alt |
| 5,861,025 A | 1/1999 | Boudghene et al. |
| 5,891,154 A | 4/1999 | Loeffler |
| 5,911,752 A | 6/1999 | Dustrude et al. |
| 5,911,754 A | 6/1999 | Kanesaka et al. |
| 5,913,895 A | 6/1999 | Burpee et al. |
| 5,922,020 A * | 7/1999 | Klein et al. ............... 623/1.15 |
| 5,925,054 A | 7/1999 | Taylor et al. |
| 6,129,755 A | 10/2000 | Mathis et al. |
| 6,206,911 B1 | 3/2001 | Milo |
| 6,231,598 B1 | 5/2001 | Berry et al. |
| 6,241,760 B1 | 6/2001 | Jang |
| 6,273,911 B1 | 8/2001 | Cox et al. |
| 6,309,414 B1 * | 10/2001 | Rolando et al. ........... 623/1.15 |
| 6,342,067 B1 | 1/2002 | Mathis et al. |
| 6,464,720 B2 | 10/2002 | Boatman et al. |
| 6,485,509 B2 | 11/2002 | Killion et al. |

FOREIGN PATENT DOCUMENTS

| | | |
|---|---|---|
| EP | 744164 | 5/1996 |
| WO | WO 96 12517 | 5/1996 |
| WO | WO 96 13228 | 5/1996 |
| WO | WO 96 26689 | 9/1996 |
| WO | WO 97 09932 | 3/1997 |
| WO | WO 98 07387 | 2/1998 |
| WO | WO 98 07388 | 2/1998 |
| WO | WO 98 07390 | 2/1998 |
| WO | WO 98 09583 | 3/1998 |
| WO | WO 98 12988 | 4/1998 |
| WO | WO 98 17204 | 4/1998 |

OTHER PUBLICATIONS

Ulrich Sigwart, *"An Overview of Intravascular Stents: Old and New"*, (1994), 803–815.

Ruth Haas, *"Implantation and Imaging of Coronary Stents"*, (1994), 233–244.

C Mikaelsson, et al., *"Nonsuture end–to–end Microvascular Anastomosis Using Intravascular Stents,"* (1996), 36–39.

* cited by examiner

DEFORMABLE SCAFFOLDING MULTICELLULAR STENT

This application is a divisional of application Ser. No. 09/933,295, filed Aug. 20, 2001, now U.S. Pat. No. 6,613,081 which is a divisional of application Ser. No. 09/089,032, filed Jun. 2, 1998, now U.S. Pat. No. 6,330,884 which is a continuation-in-part of application Ser. No. 08/970,694, filed Nov. 14, 1997, now U.S. Pat. No. 6,432,127, the disclosure of which is expressly incorporated herein by reference.

FIELD OF THE INVENTION

The present invention relates generally to implantable devices for use within the cardiovascular system, and more particularly to deformable prostheses for implantation within and/or between blood vessels, and to methods of using them.

BACKGROUND

A variety of stents are known for use within arteries of a patient for treating stenoses, strictures, aneurysms, and the like. For example, a stent may be implanted within a partially occluded region of an artery to retain stenotic material beneath the stent and/or to open the lumen of the artery to improve blood flow therethrough.

Stents generally have a substantially cylindrical shape and are expandable between a contracted condition for facilitating delivery and an enlarged condition for engaging the vessel wall after deployment within the artery. Stents may be self-extending, i.e., they may be biased to the enlarged condition but restrained in the contracted condition during delivery, for example within a sheath. Alternatively, stents may be substantially malleable or plastically deformable, i.e., the stent may be delivered in a contracted condition on a delivery catheter, and expanded by a balloon on the delivery catheter, until it plastically deforms into the enlarged condition.

Many stents include a plurality of segments or cells that are separated by one or more connectors extending between adjacent segments. For example, U.S. Pat. No. 5,104,404 discloses an expandable stent that includes a number of cylindrical segments, with single hinges connecting adjacent segments. Because of the rigidity of the individual segments of the stent, the hinges are intended to provide articulation between the adjacent segments.

When the stent is deployed within a curved portion of a vessel, the individual segments substantially resist bending to conform to the curvature of the vessel. The articulation provided by the hinges allows some conformity with the curvature of the vessel; however, the hinges may create gaps between the segments and/or may cause the segments to overlap one another. Material, such as stenotic material on the vessel wall, may extend through the gaps into the vessel lumen, possibly obstructing blood flow and/or breaking loose and traveling downstream where they may cause substantial damage to the patient being treated.

To reduce the likelihood of gaps occurring, some stents provide a number of connectors extending between adjacent segments. Increasing the number of connectors substantially, however, may increase the rigidity of the stent, which may cause problems during stent delivery. For example, when the stent is being delivered along a circuitous arterial path, the rigidity of the stent, particularly in its contracted condition, may impair advancement of the stent around tight bends in the artery.

Alternatively, some stents may include flexible connectors that are deformed when the segments are expanded to the enlarged condition. The resulting connectors may deform substantially to become part of the stent structure, i.e., they may deform substantially such that they lose their flexibility and are then unable to accommodate transverse bending forces.

In addition, some known stents have substantial gaps within the individual segments themselves or between the connectors, and so may not effectively "scaffold" the underlying vessel wall, i.e., may not support the vessel wall to maintain a desired open lumen cross-section and/or may expose material extending from the vessel wall into the bloodstream. Initially, stents in their contracted condition may have substantially few gaps within the individual segments, i.e., peripherally about the circumference of the segments. When the stents are expanded to their enlarged condition, however, substantial gaps may be created at one or points along the circumference either within the segments, due to the design of the segments or to uneven expansion of the individual segments, or between the connectors.

The risk of uneven radial expansion may be particularly problematic with respect to balloon-expandable stents due to the nature of the balloons generally used. Balloon-expandable stents are typically manually compressed onto an inelastic balloon provided on the delivery catheter. Because of its inelasticity, the balloon is typically rolled circumferentially or otherwise wrapped around the catheter before the stent is placed over it, thereby attempting to ensure that the balloon is not snagged or damaged during delivery or deployment of the stent.

Once the stent is delivered intraluminally to a desired region within a vessel, the balloon is inflated to expand the stent to its enlarged condition. As the balloon unwraps during inflation, it may subject the stent to radial forces that are not substantially even along the length and/or the circumference of the stent. More particularly, some regions of the balloon may expand more quickly than other regions that have not yet fully unwrapped, causing localized heightened radial forces which may cause uneven radial expansion of the stent. Because of the unevenly distributed forces, a portion of the circumference of the stent overlying an initially unwrapped region of the balloon may be expanded greater than an adjacent portion where the balloon has not yet fully unwrapped. This may substantially increase the risk of over-expanding portions of the stent, and thereby creating gaps in the over-expanded portions.

In an effort to provide a uniform enlarged condition, stents generally have a substantially uniform pattern extending about the circumference of the individual segments, and generally have segments of equal lengths. Because of the uneven radial forces which may be encountered during expansion, however, these stents may not expand substantially uniformly despite the intended result of their uniform designs. This problem may be further exacerbated because individual stents are generally intended to be expanded to a range of potential enlarged sizes, for example, between 3.0 mm and 5.5 mm. While at the upper end of the range, the radial forces may become more even and expand the stent more uniformly, the stent may be prone to uneven expansion at the lower end of the range, where localized heightened radial forces are more likely to occur.

Accordingly, it is believed that there is a need for stents which more effectively scaffold the vessel wall and/or which substantially evenly engage vessel walls, particularly within curved vessel regions, and for methods and systems using such stents.

SUMMARY OF THE INVENTION

The present invention is directed to implantable devices for use within body passages, particularly within the cardiovascular system, and more particularly to deformable prostheses for implantation within and/or between blood vessels, and to methods of using them to create and/or maintain connections between adjacent blood vessels.

In one aspect of the present invention, a stent is provided for implantation within a body passage that includes a plurality of expandable segments defining a circumference and a longitudinal axis, and a connector extending between adjacent segments. Each segment includes an alternating pattern of curvilinear elements extending about the circumference.

In a preferred embodiment, the alternating pattern includes a first set of curvilinear elements having a first resistance to expansion and a second set of curvilinear elements having a second resistance to expansion substantially higher than the first resistance to expansion. Consequently, each segment is expandable between a contracted condition, a first or intermediate expanded condition, and a second or final expanded condition. Preferably, the first expanded condition is achieved when a radial force exceeding the first resistance to expansion is applied to the segment, and the second expanded condition is achieved when a radial force exceeding the second resistance to expansion is applied to the segment.

More preferably, the first and second sets of curvilinear elements are substantially "U" shaped elements having first and second longitudinal lengths, respectively, the second longitudinal length being substantially less than the first longitudinal length. The substantially "U" shaped elements of the first and second sets of curvilinear elements are connected to one another to define a substantially sinusoidal pattern extending circumferentially along the segments, the sinusoidal pattern having an alternating amplitude defined by the first and second longitudinal lengths. Alternatively, the substantially "U" shaped elements may have first and second thicknesses or diameters, wherein the first thickness is substantially less than the second thickness.

In addition, the connector preferably includes a curve extending at least partially circumferentially along the circumference defined by the plurality of segments. More preferably, the connector defines a sinusoidal shape adapted to extend and compress axially substantially evenly when the adjacent segments are subjected to a predetermined bending force. Although the connector may extend and compress, the connector preferably does not deform substantially when the stent is expanded, i.e., the connector remains substantially stationary and distinct from the adjacent segments and does not become part of the cellular structure itself. Furthermore, the connector preferably includes a pair of connectors located opposite one another on the circumference for facilitating articulation of the adjacent segments substantially transverse about the longitudinal axis.

Thus, an important aspect of the present invention is to provide a stent that includes a substantially tubular member plastically deformable between contracted and enlarged conditions, including a plurality of cylindrical segments and connectors for facilitating articulation of the adjacent cylindrical segments about the longitudinal axis, for example, when the stent is bent during delivery in a curved body passage and/or that substantially uniformly scaffolds the wall of the body passage.

In another aspect, the present invention is directed to a device for delivering an expandable stent, such as that previously described, to a site within a patient's body. The device includes an elongate member having proximal and distal ends, a nose cone on the distal end, and an expandable member on the elongate member proximate to the nose cone for receiving an expandable stent thereon. The nose cone has a widened portion and a tapered distal tip to facilitate insertion along a body passage.

The stent delivery device also preferably includes an outer sheath slidable over the elongate member, the outer sheath including a lumen for receiving the elongate member therethrough. The outer sheath includes a distal end having a diameter substantially similar to the widened portion of the nose cone for substantially sealing the lumen when the distal end of the outer sheath engages the widened portion of the nose cone and/or to provide a substantially smooth transition therebetween to facilitate advancement of the stent delivery device through the body passage. In addition, the outer sheath may include one or more perfusion holes extending between an outer surface of the outer sheath and the lumen for allowing continued perfusion of fluid along the body passage during stent delivery. The nose cone may also include perfusion holes proximal and distal of the widened portion.

In addition, the stent delivery device also may include a shoulder on the elongate member proximate the expandable member. The shoulder preferably has a blunt distal edge for engaging a proximal end of an expandable stent received on the expandable member to prevent substantial proximal movement of the expandable stent. The shoulder may also include a substantially tapered proximal edge to facilitate withdrawal of the elongate member from a body passage.

The device may be used in a method for implanting a prosthesis or stent within a curved region of a body passage, the stent including a plurality of cylindrical segments and a plurality of connectors extending between adjacent segments, as previously described. The stent is placed in a contracted condition on a distal end of a stent delivery device, the distal end of the stent delivery device is advanced along the body passage, and the stent is positioned within the curved region. The stent is then expanded, first to an intermediate enlarged condition to substantially eliminate localized radial forces, and then further to a final enlarged condition, the circumferential pattern of alternating curvilinear elements expanding substantially evenly about a circumference of the stent to scaffold the curved region. The stent delivery catheter may then be withdrawn from the body passage, leaving the stent substantially permanently implanted within the curved region.

More preferably, the stent delivery device is used in a method for delivering an expandable stent to a selected delivery site within a patient's body, for example, within the cardiovascular system. The stent delivery device includes an elongate member having an expandable member on its distal end, a tapered nose cone, a proximal shoulder, and an outer sheath for slidably receiving the elongate member therein. The stent is placed in a contracted condition on the expandable member, and the elongate member is inserted into the outer sheath to cover the stent. The distal end of the elongate member is advanced along a body passage within the patient's body, and the stent is positioned at the selected delivery site. The outer sheath is withdrawn proximally to expose the stent at the selected delivery site, and the stent is expanded to an enlarged condition with the expandable member. The method described may be particularly useful for creating and/or maintaining a channel connecting a vein to an adjacent artery, preferably in the coronary system.

Other objects and features of the present invention will become apparent from consideration of the following description taken in conjunction with the accompanying drawings.

DETAILED DESCRIPTION OF THE PREFERRED EMBODIMENTS

Figure 1A:
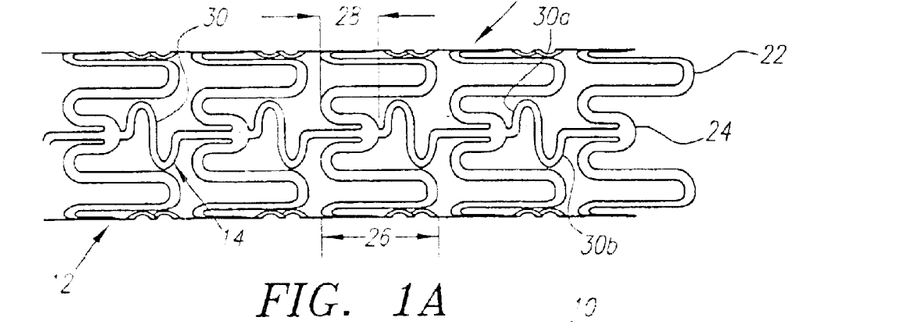
FIG. 1A is a side view of a preferred embodiment of an unexpanded stent in accordance with the present invention.
Figure 1B:
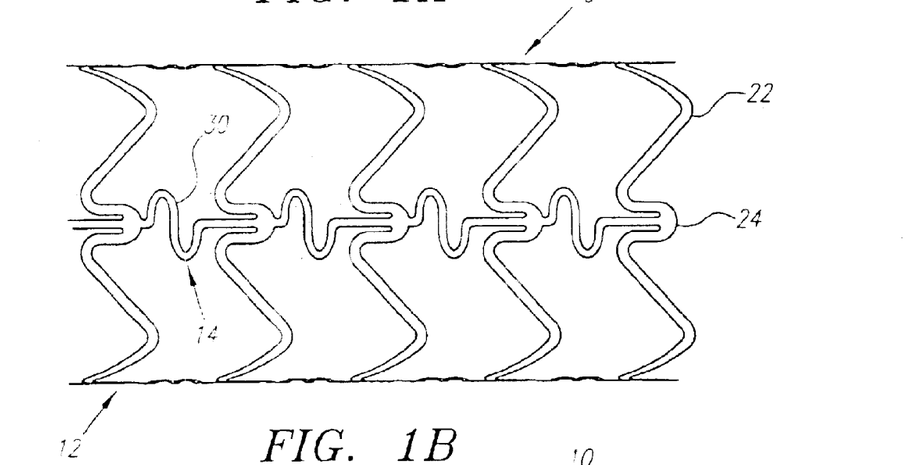
FIG. 1B is a side view of the stent of FIG. 1A expanded to a first enlarged condition.
Figure 1C:
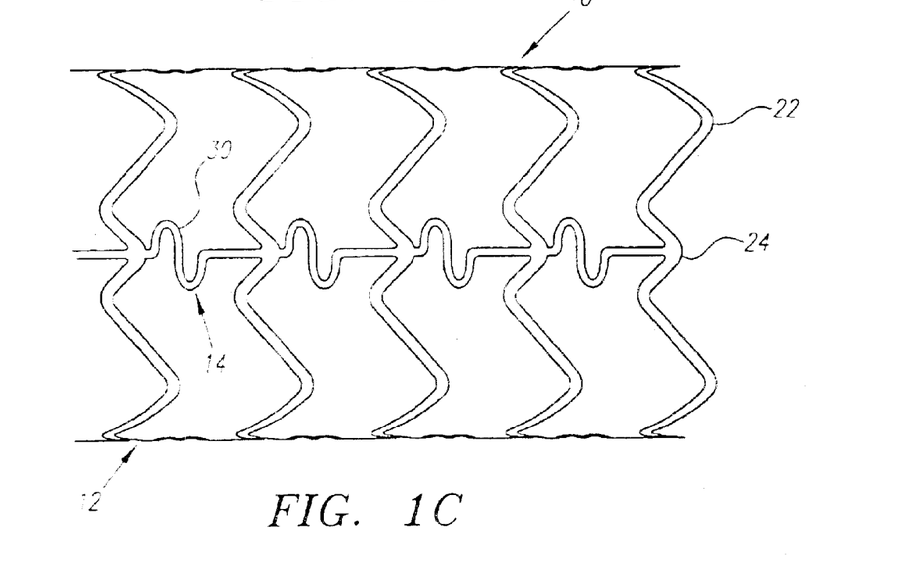
FIG. 1C is a side view of the stent of FIG. 1A expanded to a second enlarged condition.
Figures 2, 3A:
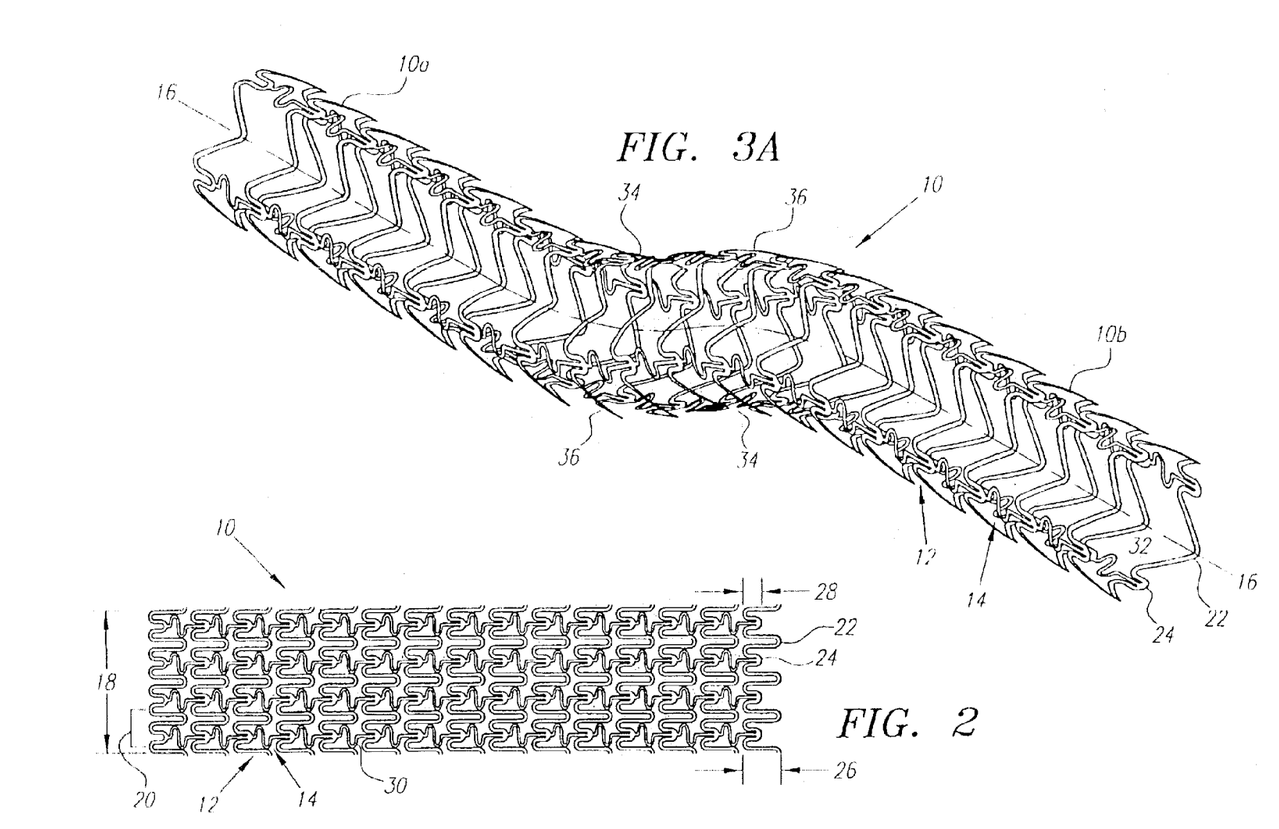
FIG. 2 is a flat view of the unexpanded stent of FIG. 1 unrolled to more clearly show the configuration of the stent elements.
FIG. 3A is a perspective view of the stent of FIG. 1B, expanded to the first enlarged condition.
Figure 3B:
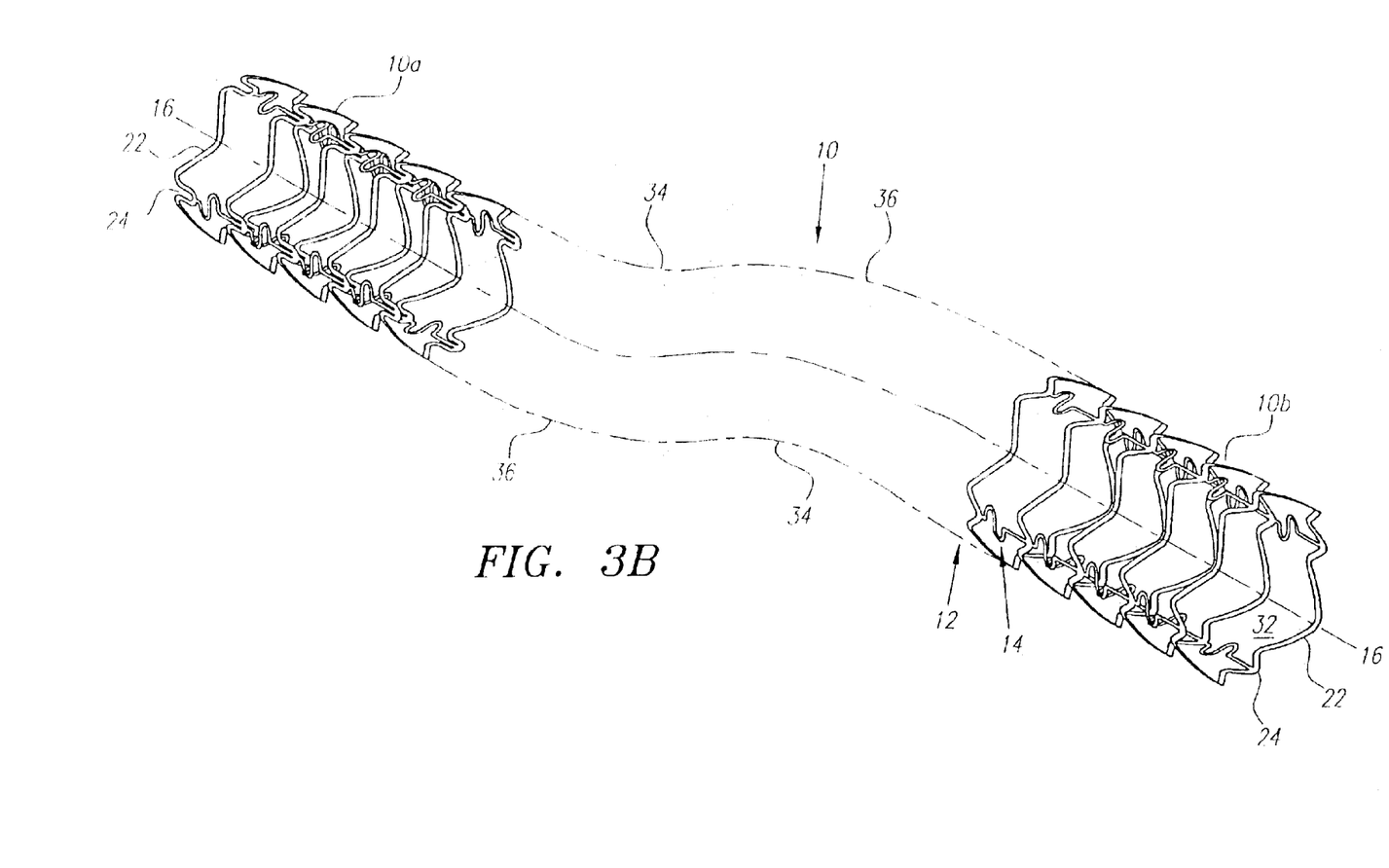
FIG. 3B is a perspective view of the stent of FIG. 1B, with a proximal portion of the stent further expanded to a second enlarged condition.

Turning now to the drawings, FIGS. 1–3 show a preferred embodiment of an implantable prosthesis or stent 10 in accordance with the present invention. Generally, the stent 10 includes a plurality of expandable cylindrical segments or "cells" 12 and a plurality of articulating connectors 14 which extend between adjacent cells 12.

Preferably, the stent 10 is an initially solid tubular member, defining a longitudinal axis 16 and a circumference 18, that is preferably formed from a substantially plastically deformable material, such as stainless steel Type 316L, tantalum, MP35N cobalt alloy, or Nitinol. The walls of the tubular member are selectively removed by high precision cutting, e.g. laser cutting, chemical etching, water jet cutting or standard tool machining, to provide the pattern of cells 12 and connectors 14 described in detail below. Alternatively, the stent may be formed from a flat sheet of material that is rolled and axially fused together after creating the pattern of cells 12 and connectors 14.

With particular reference to FIG. 2, each cell 12 includes an alternating circumferential pattern of curvilinear elements or struts 20 which extends about the circumference 18. Preferably, the alternating pattern of curvilinear elements 20 includes a first set of curvilinear elements 22, having a first resistance to expansion, that alternates with a second set of curvilinear elements 24, having a second resistance to expansion that is substantially higher than that of the first set of curvilinear elements 22. The first and second resistances to expansion correspond to the resistance of the curvilinear elements 22, 24 to plastic deformation, i.e., once first and second plastic yield strengths of the curvilinear elements 22, 24, respectively, are exceeded. Alternatively, more than two sets of curvilinear elements may be provided in the circumferential pattern, if the sets are alternated to provide a cyclical pattern about the circumference 18.

More preferably, the first and second sets of curvilinear elements 22, 24 are substantially "U" shaped elements, extending substantially parallel to the longitudinal axis 16, connected to one another to form a continuous alternating amplitude sinusoidal or "zigzag" segment that extends about the circumference 18 of the cells 12. The first set of curvilinear elements 22 has a first longitudinal length or "amplitude" 26 that is substantially longer than a second longitudinal length or amplitude 28 of the second set of curvilinear elements 24, thereby providing a longer relative lever arm that results in the lower resistance to radial expansion, as will be appreciated by those skilled in the art. In a preferred form, the first longitudinal length is about 0.045 inches, and the second longitudinal length is about half the first longitudinal length.

In an alternative form, the first and second sets of curvilinear elements 22, 24 may have similar longitudinal lengths, but may have different thicknesses or diameters (not shown). For example, the first set of curvilinear elements may have a first thickness that is substantially smaller than a second thickness of the second set of curvilinear elements, thereby providing the first and second resistances to expansion, respectively. Alternatively, a combination of different shapes, lengths and/or thicknesses may be provided for the first and second set of curvilinear elements that result in the first and second resistances to expansion, as will be appreciated by those skilled in the art.

Due to the differences in resistances to expansion of the first and second sets of curvilinear elements 22, 24, the cells 12 may be expandable between a contracted condition (FIG. 1A), an intermediate or first expanded condition (FIG. 1B), and a final or second expanded condition (FIG. 1C). The first expanded condition is achieved when a radial force at least as great as the first plastic yield strength is applied to the cells 12, and the second expanded condition is achieved when a radial force at least as great as the second plastic yield strength is applied to the cells 12, as is described more particularly below.

Extending between the cells 12, the connectors 14 generally include a curve that extends at least partially circumferentially along the circumference 18 of the stent 10, i.e., substantially transverse to the longitudinal axis 16. In a preferred embodiment, the connectors 14 define a sinusoidal shape 30. The sinusoidal shape 30 is adapted to expand and contract substantially evenly parallel to the longitudinal axis 16 when the adjacent cells 12 are subjected to bending.

In addition, the sinusoidal shape 30 also maximizes surface engagement of a body passage. The transverse portions 30a, 30b extend substantially transversely with respect to the longitudinal axis 31, thereby providing additional circumferential scaffolding to minimize gaps circumferentially between the connectors 14 which may otherwise result due to the smaller length of the second set of curvilinear elements 24.

Preferably, the connectors 14 are provided in pairs located opposite one another about the circumference 18 of the cells 12, and more preferably four connectors 14 are provided that are evenly spaced about the circumference 18 between each pair of adjacent cells 12. When the stent 10 is subjected to bending, the pairs of connectors 14 facilitate articulation of the adjacent cells 12, thereby resulting in a substantially uniform cross-section interior lumen 32 within the stent 10 that substantially scaffolds the vessel wall and minimizes the creation of gaps between adjacent cells 12.

When the stent 10 is bent substantially transversely with respect to the longitudinal axis 16, as shown in FIGS. 3A and 3B, it is preferred that an outer radiused portion 36 of the stent 10 extend longitudinally and an inner radiused portion 34 compress longitudinally to minimize any overall change in length of the stent 10. The sinusoidal shape 30 of the pair of connectors 14 facilitates this by providing a similar resistance to deformation when subjected to either tensile or compressive forces. Thus, a pair of connectors 14 on the outer and inner portions 34, 36 of a bend may extend and compress longitudinally substantially evenly, thereby facilitating articulation of the stent 10 substantially evenly about the longitudinal axis 16 and substantially eliminating the creation of gaps between the adjacent cells 12.

The substantially "S" shape of the stent 10 shown in FIGS. 3A and 3B may be a particularly useful configuration for the final enlarged condition. In this configuration, the stent 10 may be used to maintain a channel between adjacent body passages, such as adjacent blood vessels (not shown), as described further below. More particularly, as shown in FIG. 3B, the stent 10 may be expanded to the first enlarged condition on a distal end 10a, and to the second enlarged condition on a proximal end 10b to facilitate placement between adjacent blood vessels having different diameters, e.g. between an artery and a vein, respectively (not shown). Additional information on procedures for creating and/or maintaining channels between adjacent body passages may be found in U.S. patent application Ser. No. 08/970,694 filed Nov. 14, 1997, the disclosure of which is expressly incorporated herein by reference.

Returning to the cells 12, the alternating pattern 20 of curvilinear elements described above is an important feature of a stent 10 in accordance with the present invention, which may be illustrated by generally describing the deployment of the stent 10. The stent 10 is delivered to a selected delivery site within a body passage, such as a blood vessel (not shown), using a stent delivery device, such as that shown in FIGS. 5A and 5B and designated as 100. The stent delivery device 100 includes an elongate catheter body or tubular member 102 having a distal end 104 adapted for insertion into a body passage.

A balloon 108 or other expandable member is attached to or otherwise provided on the catheter body 102, preferably with a marker 106, such as a radiopaque marker, on the catheter body 102 in a predetermined relationship with the balloon 108. The balloon 108 is preferably formed from an inelastic material, such as polyethylene, that expands to a diameter preselected to correspond to the diameter of the body passage into which the stent 10 is to be implanted. Because of its inelasticity, the uninflated balloon 108 is typically wrapped around the elongate member 102, e.g., by rolling the balloon 108 circumferentially.

The stent 10 is compressed over the balloon 108, and delivered during a surgical procedure, such as the preferred method described below. Once the stent 10 is advanced and properly positioned at the delivery site, the balloon 108 is inflated to expand the cells 12 of the stent 10 (not shown in FIGS. 5A and 5B). As the balloon 108 inflates, it may not unwrap substantially uniformly, causing the radial forces applied to the cells 12 to be initially localized, i.e., certain portions of the cells 12 may be expanded more than others.

Because the first set of curvilinear elements 22 (not shown in FIGS. 5A and 5B) of the cells 12 has a lower resistance to expansion than the second set of curvilinear elements 24, the first set of curvilinear elements 22 expands more quickly than the second set of curvilinear elements 24, thereby expanding the cells 12 to their intermediate enlarged condition (FIG. 1B). After the balloon 108 is substantially unwrapped, it may be inflated further, thereby applying a substantially uniform radial force to the cells 12. When this substantially uniform radial force is applied to the alternating resistances to expansion of the first and second sets of curvilinear elements 22, 24, the radial force of the balloon 108 is distributed substantially circumferentially evenly about the circumference of the cells 12, thereby expanding the cells 12 to the final enlarged condition (see FIG. 1C) while substantially eliminating localized over-expansion that can create gaps within the cells 12.

In addition, although the connectors 14 may extend and compress as the adjacent cells 12 are expanded, e.g., within a curved body passage, the connectors 14 preferably do not deform substantially. Stated differently, the connectors 14 preferably remain substantially stationary and distinct from the adjacent segments 12, i.e., retaining a substantially sinusoidal shape, and do not become part of the cellular structure of the stent 10.

Turning to FIGS. 4A–4I and 6A–6D, a system and method for delivering a stent 10 in accordance with the present invention is illustrated. In a preferred embodiment, shown particularly in FIG. 6A, a stent delivery device 200 for delivering an expandable stent 10 is provided, which includes an elongate catheter body 202 with an expandable balloon 208, a nose cone 212, a shoulder 216 thereon, and an outer sheath 220. The catheter body 202 has a proximal end 203, a distal end 204, and a lumen 210 extending therebetween for directing the catheter body 202 over a guide wire 110 (FIGS. 4A–4I). The materials and dimensions of the catheter body 202 are otherwise similar to conventional catheter devices, as will be appreciated by those skilled in the art.

The nose cone or dilator 212 is attached to the distal end 204 of the catheter body 202, and has a tapered distal tip 216 to facilitate advancement along a body passage and/or to dilate partially occluded regions of the body passage. The nose cone 212 may be provided from substantially flexible and or resilient material, such as Pebax®, polyurethane, polyethylene, or nylon, adapted to minimize damage to tissue during advancement of the stent delivery device 200 within the body passage. The nose cone 212 has a widened portion 214, preferably with a diameter of not more than about 6 French, thereby allowing percutaneous insertion into a blood vessel, such as into a patient's vasculature. The nose cone 212 may have a tapered proximal end 218, or alternatively a substantially blunt proximal end (not shown) for engaging the distal edge 36 of the stent 10 to prevent substantial distal movement of the stent 10 with respect to the catheter body 202.

The balloon 208 is attached to the catheter body 202 proximate to the nose cone 212. The balloon 208 preferably has an annular shape that is formed from a substantially inelastic material, such as polyethylene or nylon, and preferably has a predetermined inflated diameter selected to correspond to the size of the stent 10 in its enlarged condition and/or to the body passage into which the stent 10 is to be implanted, and length selected to correspond to the length of the stent 10, as will be appreciated by those skilled in the art. The interior of the balloon 208 communicates with an inflation lumen (not shown) which extends proximally from the distal end 204 of the catheter body 202 to a source of inflation media, such as saline (not shown). Alternatively, other inflatable or mechanically expandable members may be provided instead of the balloon 208.

The shoulder or backstop 213 is provided on the catheter body proximate the balloon 208. The shoulder 213 has a substantially blunt distal edge 214 for engaging a proximal end 36 of the stent 10 received on the balloon 208 to prevent substantial proximal movement of the stent 10. The shoulder 213 also preferably has a tapered proximal edge 216 to facilitate withdrawal of the catheter body 202 from within a body passage. The shoulder 213 may be integrally formed as part of the catheter body 202 or it may be a separate attached member.

The catheter body 202 may also include one or more markers, such as the radiopaque marker 206, thereon. The marker 206 preferably has a predetermined relationship with the balloon 208, and consequently to the stent 10 placed thereon, to facilitate positioning of the stent 10 at the delivery site. For example, the marker 206 may be placed at a midpoint of the balloon 208 as shown, thereby allowing the stent 10 to be centered across a body passage. Alternatively, a marker may be provided adjacent to either end of the balloon 208, i.e. adjacent the proximal end 34 and/or the distal end 36 of the stent. In a further alternative, the nose cone 212 and/or the shoulder 213 may be provided from a radiopaque material or may be marked at a predetermined location thereon.

The outer sheath 220 is an elongate member having a proximal end 222, a distal end 224, and a lumen 226 therein, that is slidable over the catheter body 202, i.e., the catheter body 202 may be slidably received within the lumen 226 in the outer sheath 220. Preferably, the distal end 224 of the outer sheath 220 is tapered to facilitate advancement along a body passage, and more preferably, the distal end 224 has an inner diameter similar to the widened portion 214 of the nose cone 212. Thus, when the catheter body 202 is received within the outer sheath 220, the distal end 224 may engage the widened portion 214 to provide a substantially smooth surface which may facilitate advancement of the stent delivery device 200 through a body passage. In particular, the resulting smooth surface may facilitate advancement of the nose cone 212 and outer sheath 220 through a channel created between two adjacent blood vessels, with minimized risk of snagging or getting caught on loose tissue in the channel. In addition, the outer sheath 220 may engage the nose cone 212 to substantially seal the lumen 224 and thereby prevent fluid contact with the stent 10 until exposed at the delivery site.

The stent delivery device 200 may also include a handle or control mechanism 230 on the proximal end 203 of the catheter body 202. The handle 230 may include an outer housing 232 to which the proximal end 203 of the catheter body 202 is fixed, and a slider 234 slidable with respect to the housing 232, i.e., within a cavity 236 therein. The proximal end 222 of the outer sheath 220 may be attached to the slider 234, such that when a thumb grip 238 or other slider control is engaged and drawn proximally, the outer sheath 220 may be withdrawn proximally, for example, to expose the balloon 208 when a stent 10 is initially placed thereon or to expose the stent 10 at the delivery site.

Figure 4A:
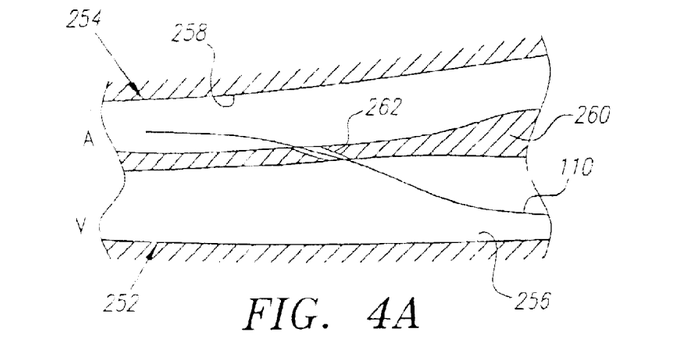
FIG. 4A is a cross-sectional side view of two adjacent blood vessels with a guide wire placed through a channel between the vessels.
Figure 4B:
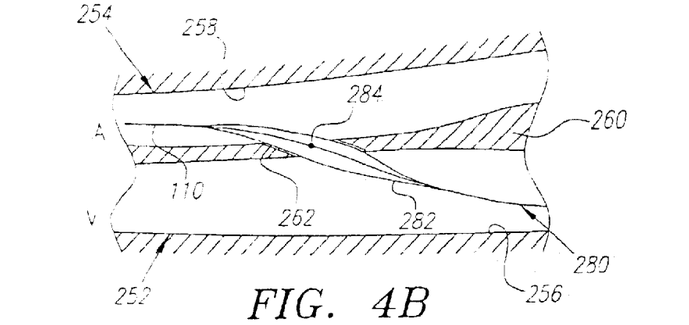
FIGS. 4B and 4C show a balloon catheter delivered over the guide wire and positioned between the vessels of FIG. 4A, with the balloon collapsed for delivery and expanded for dilating the channel, respectively.
Figure 4C:
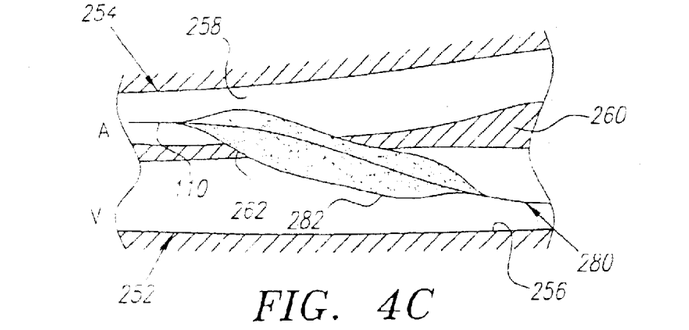
Figure 4D:
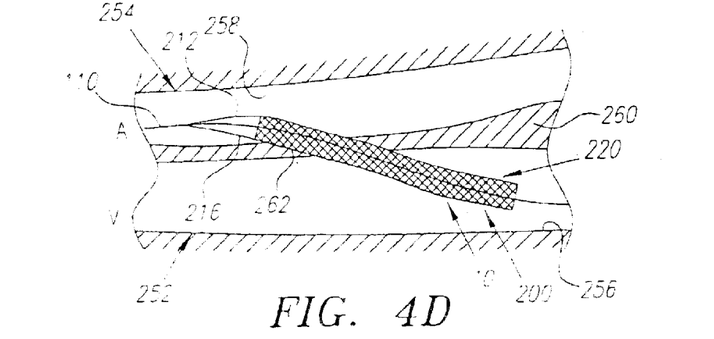
FIG. 4D shows a stent delivery device being delivered over the guide wire, after withdrawal of the balloon catheter of FIGS. 4B and 4C.
Figure 4E:
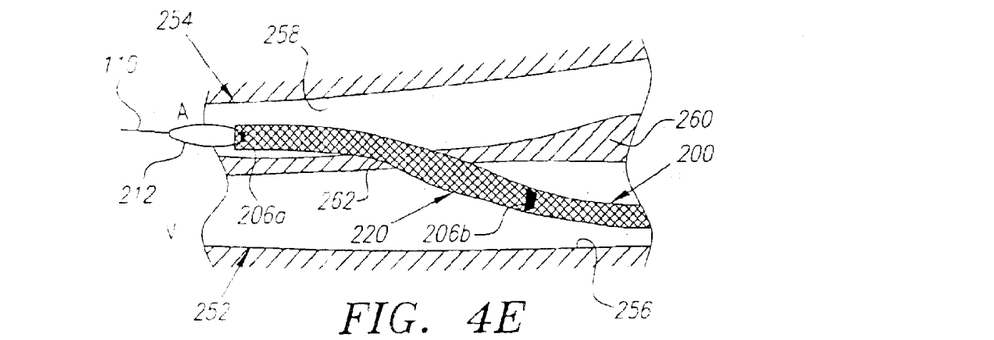
FIGS. 4E and 4F show a stent being positioned across the channel of FIG. 4D with the assistance of markers on the stent delivery device, and an outer sheath being retracted to expose the stent, respectively.
Figure 4F:
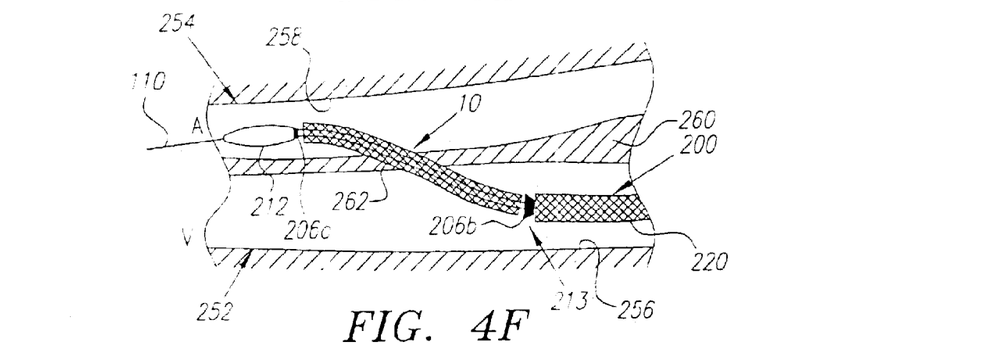
Figure 4G:
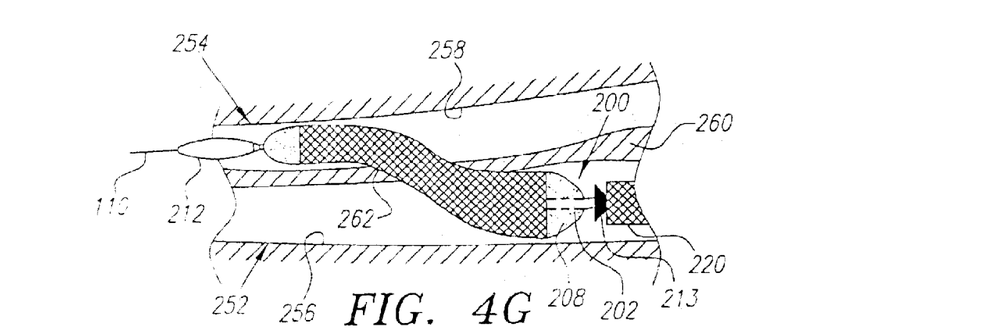
FIGS. 4G and 4H show a balloon on the stent delivery device of FIGS. 4E and 4F being inflated to expand the stent to its enlarged condition, and being deflated to facilitate withdrawal of the stent delivery device, respectively.
Figure 4H:
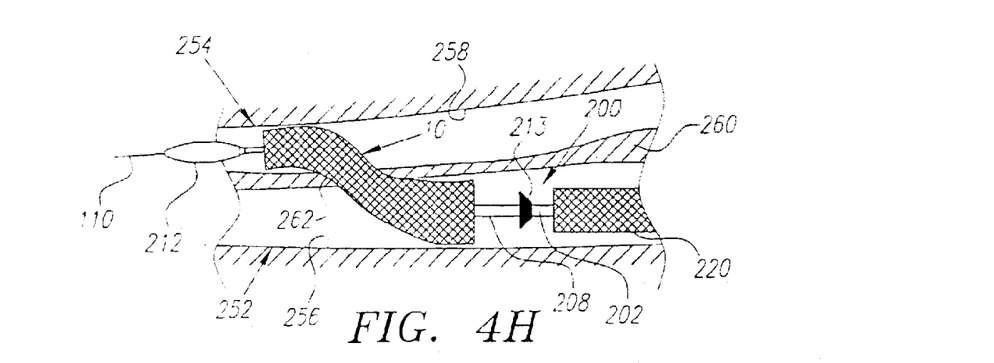
Figures 4I, 5A, 5B, 6A:
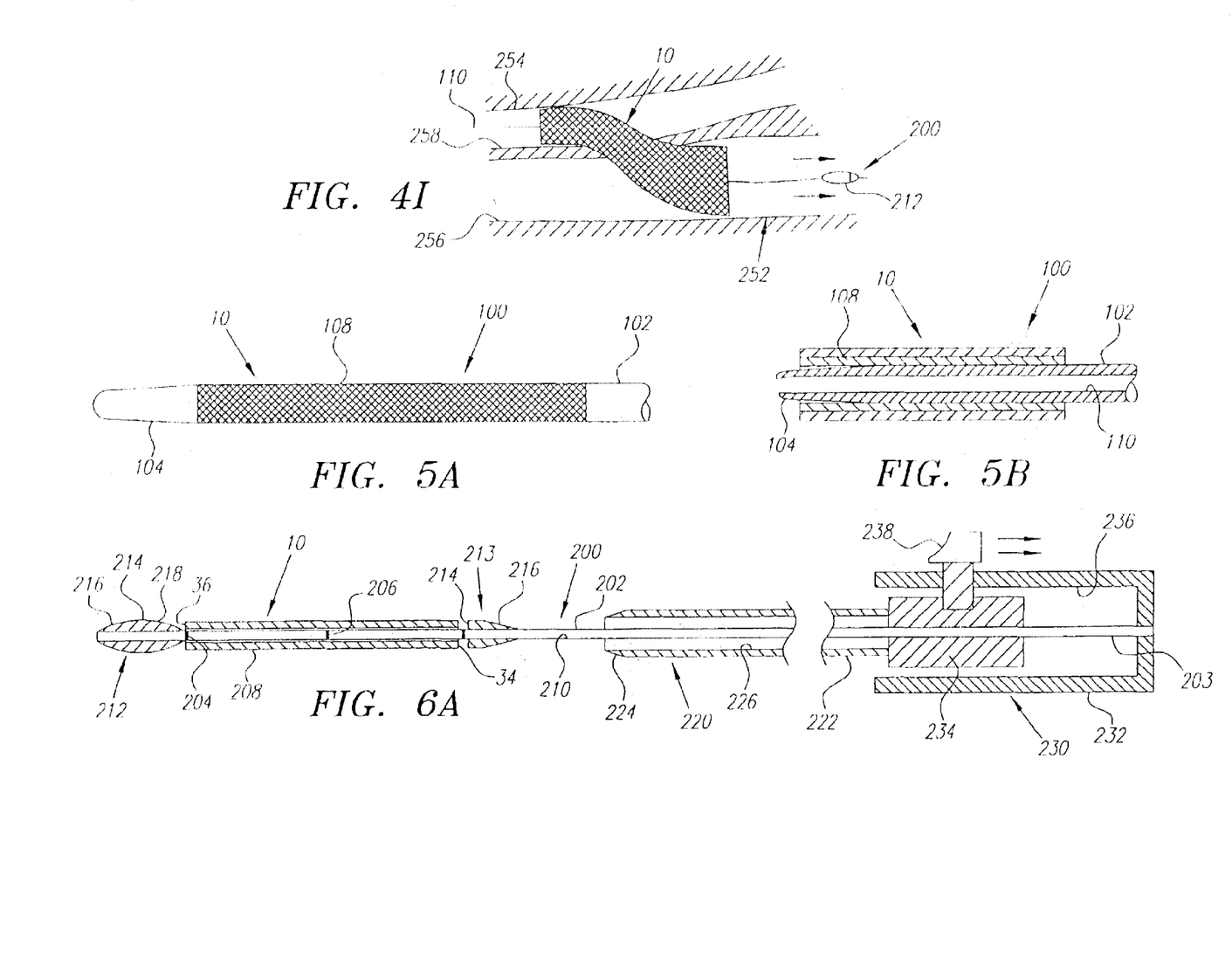
FIG. 4I shows the stent delivery device of FIGS. 4G and 4H being withdrawn, leaving the stent in place across the channel.
FIG. 5A is a side view of a preferred embodiment of a stent delivery device, with a stent placed in a collapsed condition over a balloon on the stent delivery device.
FIG. 5B is a cross-sectional side view the stent delivery device of FIG. 5A.
FIG. 6A is a cross-sectional side view of another preferred embodiment of a stent delivery device with a nose cone, a backstop, and an outer sheath.

With particular reference to FIGS. 4A–4I and 6A, the stent delivery device 200 may be used in a method for creating and/or maintaining a channel between adjacent body passages, such as a channel 262 between a coronary vein 252 and a coronary artery 254. A guide wire 110 is percutaneously introduced into a passage in a patient's body, such as a femoral vein, advanced into the coronary vein 252, and placed through the intervening tissue 260 into the adjacent coronary artery 254 to provide a channel 262 (FIG. 4A).

A balloon catheter 280 is advanced over the guide wire 110 until a marker 284 on the balloon catheter 280 is positioned in a predetermined relationship with the channel 262, e.g., the marker 284 may be centered under a balloon 282 on the balloon catheter 280 (FIG. 4B). The balloon 282 is then inflated to dilate the channel 262, i.e., to push the surrounding tissue 260 adjacent the channel 262 away and provide a cross-section sufficiently large to allow substantially unimpaired blood flow between the artery 254 and the vein 252 (FIG. 4C). The balloon 280 may then be deflated, and the balloon catheter 280 withdrawn over the guide wire 110 and out of the body.

Alternatively, other methods may be used to enlarge the channel 262 instead of using the balloon catheter 280. For example, the channel 262 may be debulked by removing intervening tissue 260 using energy, such as laser or radio frequency (RF) energy, or by cutting or slicing through the intervening tissue 260, with over-the-guide wire instruments, until a desired size channel 262 is produced. In further alternatives, other dilation devices may be used, such as mechanically expandable members, or the nose cone 212 of the stent delivery catheter 200, as described below.

A stent 10 having a predetermined length and enlarged condition diameters is selected to correspond with the configuration of the channel 262, the artery 254 and/or the vein 252. The stent 10 may be preselected if the delivery site is known prior to the commencement of the procedure, or the stent 10 may be selected once the site for the channel 262 is selected during the course of the procedure. The stent 10 is then placed on a stent delivery device 200, as shown in FIG. 6A. Generally, the stent delivery device 200 is selected to correspond to the selected stent 10 and delivery site, i.e., based on the diameter of the catheter body 202, the inflated balloon 208 and/or the outer sheath 220.

The balloon 208 may be rolled or otherwise wrapped around the catheter body 202, and the stent, in its contracted condition, is placed over the balloon 208, for example, by manually compressing the stent 10 onto the balloon 208. The outer sheath 220 may then be advanced over the catheter body 202 until its distal end 224 substantially engages the nose cone 212, thereby substantially sealing the stent 10 within the lumen 226 in the outer sheath 220. Alternatively, the stent 10 may be sufficiently secured to the catheter body 202 such that the stent 10 may be delivered without the outer sheath 220, as shown, for example, in FIGS. 5A and 5B, as will be appreciated by those skilled in the art.

The stent delivery device 200 is then advanced over the guide wire 110 until the nose cone 212 passes through the channel 262 (FIG. 4D). The tapered distal tip 216 of the nose cone 212 facilitates the advancement of the stent delivery catheter 200 through the channel 262. The widened portion 214 of the nose cone 212 may have a size larger than the channel 262 to further dilate the channel 262 as the nose cone 212 is advanced therethrough. Alternatively, the nose cone 212 may be used to dilate the channel 262 in place of the balloon catheter 280. For example, as the nose cone 212 is advanced through the channel 262, the intervening tissue 260 may be pushed substantially away to dilate the channel 262, although it may be necessary to withdraw and advance the nose cone 212 multiple times to effectively dilate the channel 262.

Figure 6B:
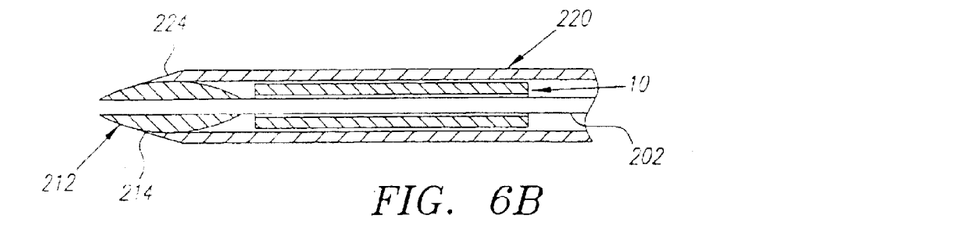
FIG. 6B is a cross-sectional side view of the distal end of the stent delivery device of FIG. 6A, with the outer sheath substantially engaging the nose cone.
Figure 6C:
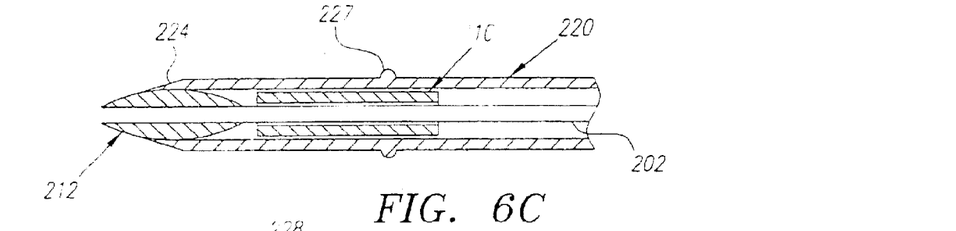
FIG. 6C is an alternative embodiment of the stent delivery device of FIG. 6B, with a tactile indicator protrusion on the outer sheath.
Figure 6D:
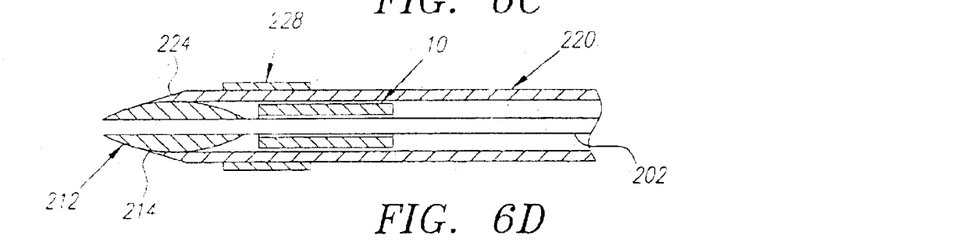
FIG. 6D is another alternative embodiment of the stent delivery device of FIG. 6B, with a dilation balloon on the outer sheath.

In a further alternative, shown in FIG. 6D, the outer sheath 220 may include a dilation balloon 228 proximate its distal end 224. The dilation balloon 228 may be similar to the dilation balloon 280 described previously, but attached around the outer sheath 220, preferably such that the outer sheath 220 and unexpanded balloon 228 have a diameter of about twelve French or less. When the outer sheath 220 and the nose cone 212 are advanced and contact the undilated channel 262, or other partial obstruction, the balloon 228 may be inflated to open the body passage, and then deflated to allow further advancement or withdrawal.

The substantially smooth transition between the outer sheath 220 and the nose cone 212 is an important feature, which may minimize snagging or otherwise damaging the surrounding tissue 260 with the distal end 224 of the outer sheath 220. The smooth transition may also minimize catching the distal end 224 of the sheath 220 on loose tissue, a lesion or other constrictions in the body passage which may prevent further advancement of the stent catheter device 200.

In addition, because the outer sheath 220 substantially contains the stent 10 therein, the outer sheath 220 may also substantially minimize potential damage to vessel walls and the tissue 260 surrounding the channel 262, which may otherwise occur if an exposed stent 10 is advanced therethrough. The outer sheath 220 may also substantially protect the stent 10 itself during advancement over the guide wire 10. For example, the outer sheath 220 may protect the stent 10 from being dislodged from the stent delivery device 200 prematurely, i.e., at a location other than the intended delivery site. Thus, the outer sheath 220 may substantially eliminate the risk of emergency surgical procedures to recover loose stents 10. Alternatively, if the outer sheath 220 is eliminated, the blunt edge 214 of the shoulder 213 and/or of the nose cone 212 may sufficiently protect the stent 10, and prevent substantial axial movement of the stent 10 as it is being advanced through the body passage.

The stent 10 may be positioned across the channel 262 with the aid of markers 206a, 206b. Preferably, the markers 206a, 206b are radiopaque, such that they may be viewed using fluoroscopy, or other external imaging methods. The markers 206a, 206b, shown in FIGS. 4E and 4F, for example, are provided on the nose cone 212 and the shoulder 213 to approximate the location of the proximal and distal edges 34, 36, respectively, of the stent 10.

Alternatively, as shown in FIG. 6B, the outer sheath 220 may include one or more protrusions 227 for assisting in positioning the stent 10 across the channel 262 (not shown in FIG. 6B). For example, the protrusion 227 may be a substantially rounded annulus molded directly onto the outer sheath 220 at a predetermined location with respect to the stent 10, e.g., at a midpoint thereof. The protrusion 227 may allow a user to detect when the outer sheath 220, and consequently the stent 10, are properly positioned across the channel 262, for example, based upon the resistance of the protrusion 227 to advancement beyond the channel 262, which may substantially reduce the risk of over-advancing the stent 10 beyond the channel 262.

Once the stent 10 is properly positioned, the outer sheath 220 is withdrawn proximally to expose the stent 10 across the channel 262 (FIG. 4F). The balloon 208 may then be inflated, thereby expanding the stent 10 to its enlarged condition (FIG. 4G). The inflation of the balloon 208 may be performed in two steps, first by inflating the balloon 208 to a first pressure, thereby expanding the stent 10 to an intermediate enlarged condition and unwrapping the balloon 208 substantially from the catheter body 202 (not shown), and then by inflating the balloon 208 to a second higher pressure to fully expand the stent 10 to its final enlarged condition (FIG. 4G).

The balloon 208 may then be deflated (FIG. 4H), and then the stent delivery device 200 may be withdrawn over the guide wire 110 (FIG. 4I), leaving the stent 10 substantially permanently implanted across the channel 262. Preferably, the stent 10 substantially engages the lumens 256, 258 of the vein 252 and artery 254, respectively, as well as the tissue 260 surrounding the channel 262 to provide a substantially unimpaired passage for blood flow between the artery 254 and the vein 252.

In one form, the space between the cells 12 and/or between the curvilinear elements 22, 24 remains substantially open, thereby permitting fluid to pass through the circumference 18 of the stent 10 and to continue flowing along the vessel and not cross through the channel 262 into the other vessel. For example, when a coronary vein is used to bypass an adjacent occluded coronary artery, it may be desirable to continue to allow some blood flow along the coronary artery to perfuse the occluded region. Alternatively, a nonporous membrane (not shown) may be attached about the circumference 18 of the stent 10 to direct all fluid from the source vessel through the channel into the other vessel.

In an alternative method, because of differences in the diameters of the vein 252 and the artery 254, it may desirable to have the final diameter of the enlarged stent 10 vary along its length, as shown in FIGS. 3B and 4H. For example, the stent 10 may be selected such that the first or intermediate enlarged condition corresponds to the diameter of the artery 254 and the second enlarged condition corresponds to the diameter of the vein 252. The balloon 208 may have a diameter that varies along its length, e.g., the diameter may be larger on a proximal portion of the balloon 208 (not shown), to facilitate proper expansion of the stent 10. Alternatively, the balloon 208 may be used to expand the stent 10 to the first enlarged condition, using the method previously described, and then a second balloon may be advanced over the guide wire 110 to expand specific cells 12 or portions of the stent 10 to the second enlarged condition, as will be appreciated by those skilled in the art.

In another alternative, a portion of the stent 10 may be provided from a self-expanding material, e.g., heat treated Nitinol, and another portion may be provided from a malleable as previously described. For example, it may be desirable to have the proximal end 10b automatically expand when deployed to engage one vessel, while the distal end 10a may be selectively deformed to engage an adjacent vessel. Preferably, where the stent 10 is used to maintain a channel between a vein and an adjacent artery, the proximal end 10b may be self-expanding, thereby allowing the stent 10 to automatically expand to engage the wall of the vein. The proximal end 10b of the stent 10 may automatically enlarge to continuously engage the wall of the vein, thereby accommodating subsequent venous expansion which may occur over time as the vein is subjected to arterial pressure. The distal end 10a may be plastically deformed, for example, using a balloon catheter, to a desired enlarged condition, as described previously.

In another embodiment, particularly with regard to using the prosthesis 10 between two vessels to form an anastomosis therebetween, it may be desirable to form the prosthesis 10 and the resulting connection in more ovular shape than is desired during simple intraluminal placement where the prosthesis 10 may be generally circular. Elliptical connections in this particular application may promote a better physiologic response to the implant, by lessening turbulence in the blood flow and imitating a more natural vessel condition.

Figures 7A, 7B, 7C:
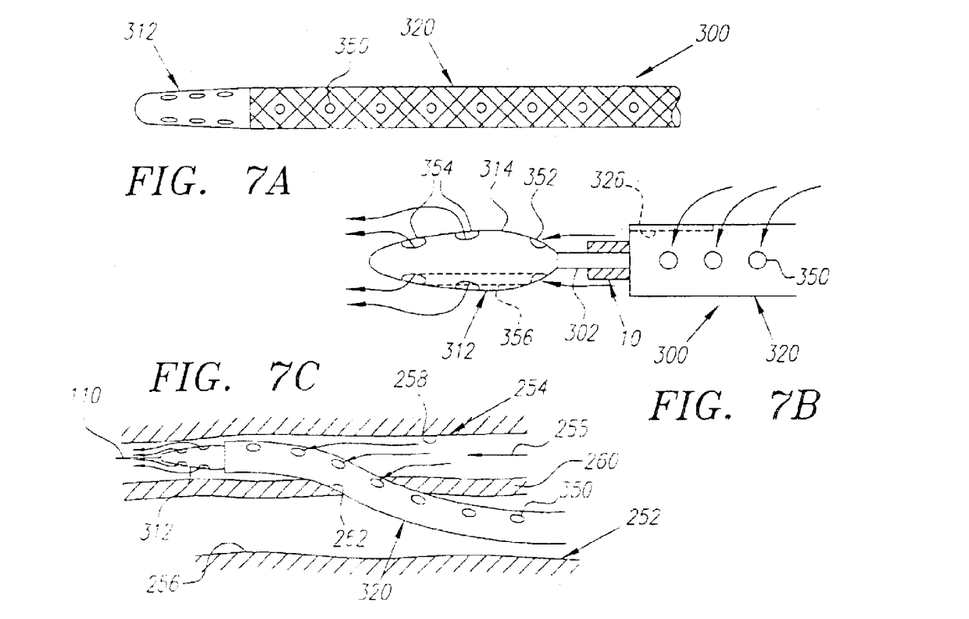
FIG. 7A is a side view of another preferred embodiment of a stent delivery device, similar to FIG. 6, with a plurality of perfusion holes through the outer sheath and the nose cone.
FIG. 7B is a detail of the distal end of the stent delivery device of FIG. 7A, showing fluid flow through the perfusion holes.
FIG. 7C is a side view of the stent delivery device of FIG. 7A placed between two adjacent blood vessels.

Turning to FIGS. 7A–7C, an alternative embodiment of a stent delivery device 300 is shown that provides continued blood perfusion during stent delivery in accordance with another aspect of the present invention. Most of the elements of this device are similar to the embodiment shown in FIG. 6A, with like elements having reference numbers increased by 100.

In particular, the stent delivery device 300 includes a catheter body 302, a nose cone 312, and an outer sheath 320. The outer sheath 320 includes one or more perfusion holes 350 that extend from its outer wall to a lumen 326 for receiving the catheter body 302 therethrough, or to a separate lumen (not shown). The nose cone 312 also includes one or more perfusion holes 352, 354 proximal and distal to the widened portion 314, with a perfusion lumen 356 (shown in phantom in FIG. 7B) extending between them.

For example, as shown in FIG. 7C, the stent delivery device 300 may be positioned across a channel 262 between a vein 252 and an artery 254, for example during the stent delivery method described above. The outer sheath 320 may substantially occlude the artery 254, such that without the perfusion holes 350, blood flow along the artery 254 would be substantially impaired. Because of the perfusion holes 350, 352, 354, however, blood may continue to travel along the artery 254, for example, first by entering the lumen 326 of the outer sheath 320 through the perfusion holes 350. The blood may then enter the proximal or inlet perfusion holes 352 in the nose cone 312, pass through the perfusion lumens 356, and then reenter the artery 254 through the distal or outlet perfusion holes 354 to continue downstream.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A prosthesis for implantation within a body passage, comprising:

a plurality of expandable segments defining a circumference and a longitudinal axis, each segment including an alternating pattern of curvilinear elements extending about the circumference, the alternating pattern including a first set of curvilinear elements having a first resistance to expansion and a second set of curvilinear elements having a second resistance to expansion substantially higher than the first resistance to expansion; and a connector extending between adjacent segments;

wherein the first and second sets of curvilinear elements comprise substantially "U" shaped elements having first and second longitudinal lengths respectively, and wherein the second longitudinal length is substantially less than the first longitudinal length.

2. The prosthesis of claim 1, wherein each segment is expandable between a contracted condition, a first expanded condition, and a second expanded condition, the first expanded condition being achieved when a radial force exceeding the first resistance to expansion is applied to the segment, the second expanded condition being achieved when a radial force exceeding the second resistance to expansion is applied to the segment.

3. The prosthesis of claim 1, wherein the substantially "U" shaped elements of the first and second sets of curvilinear elements are connected to one another to define a substantially sinusoidal pattern extending circumferentially along the segments, the sinusoidal pattern having an alternating amplitude defined by the first and second longitudinal lengths.

4. The prosthesis of claim 1, wherein the connector further comprises a pair of connectors located opposite one another on the circumference for facilitating articulation of the adjacent segments substantially transverse to the longitudinal axis.

5. The prosthesis of claim 1, wherein the connector includes a curve extending at least partially circumferentially along the circumference defined by the plurality of segments.

6. The prosthesis of claim 5, wherein the curve of the connector defines a sinusoidal shape adapted to extend and compress axially substantially evenly when the adjacent segments are subjected to a predetermined bending force.

* * * * *